US009154868B2

(12) United States Patent
Narayan et al.

(10) Patent No.: US 9,154,868 B2
(45) Date of Patent: Oct. 6, 2015

(54) NOISE CANCELLATION SYSTEM

(71) Applicant: Wolfson Microelectronics plc, Edinburgh (GB)

(72) Inventors: Renjish Kodappully Narayan, Newbury (GB); Steven Llewellyn, Thatcham (GB)

(73) Assignee: Cirrus Logic International Semiconductor Ltd., Edinburgh (GB)

( * ) Notice: Subject to any disclaimer, the term of this patent is extended or adjusted under 35 U.S.C. 154(b) by 283 days.

(21) Appl. No.: 13/773,276

(22) Filed: Feb. 21, 2013

(65) Prior Publication Data

US 2013/0216060 A1 Aug. 22, 2013

Related U.S. Application Data

(60) Provisional application No. 61/601,345, filed on Feb. 21, 2012.

(30) Foreign Application Priority Data

Feb. 21, 2012 (GB) ..................................... 1202974

(51) Int. Cl.

*A61F 11/06* (2006.01)
*G10K 11/16* (2006.01)
*H03B 29/00* (2006.01)
*H04R 1/10* (2006.01)
*H04R 3/00* (2006.01)
*H04R 5/04* (2006.01)

(52) U.S. Cl.

CPC .............. *H04R 1/1083* (2013.01); *H04R 3/005* (2013.01); *H04R 1/1016* (2013.01); *H04R 3/007* (2013.01); *H04R 5/04* (2013.01); *H04R 2410/05* (2013.01); *H04R 2430/01* (2013.01)

(58) Field of Classification Search

None

See application file for complete search history.

(56) References Cited

U.S. PATENT DOCUMENTS

| | | | |
|---|---|---|---|
| 3,819,860 | A | 6/1974 | Miller |
| 2007/0269073 | A1 | 11/2007 | Huang |
| 2010/0177904 | A1 | 7/2010 | Sung et al. |

FOREIGN PATENT DOCUMENTS

| | | | |
|---|---|---|---|
| GB | 2 441 835 | A | 3/2008 |
| GB | 2486288 | A | 6/2012 |
| WO | WO 2008/061260 | A2 | 5/2008 |
| WO | WO 2009/042635 | A1 | 4/2009 |

*Primary Examiner* — Regina N Holder

(74) *Attorney, Agent, or Firm* — Dickstein Shapiro LLP

(57) ABSTRACT

An earphone comprises an earphone body, containing a speaker, and a projection, extending from a first surface of the earphone body, for location in the entrance to the user's ear canal. The earphone body comprises a sound outlet in the first surface, for allowing sounds generated by the speaker to leave the earphone body. The projection extends from the first surface of the earphone body, adjacent to the sound outlet, and contains a sound inlet port, connected to a microphone for detecting sounds entering the ear canal. A noise cancellation system includes noise cancellation circuitry, for applying a frequency dependent filter characteristic and applying a gain to an input signal representing ambient noise, at least one of the frequency dependent filter characteristic and the gain being adaptive. The earphone then has an ambient noise microphone, and an error microphone connected to the sound inlet port.

34 Claims, 5 Drawing Sheets

NOISE CANCELLATION SYSTEM

This application claims the benefit of U.S. Provisional Application No. 61/601,345, filed on Feb. 21, 2012, the disclosure of which is herein incorporated by reference.

BACKGROUND OF THE INVENTION

1. Field of the Invention

This invention relates to a noise cancellation system, and to an earphone for use with such a system.

2. Description of the Related Art

It is known to provide a noise cancellation system, for use with a sound-reproducing device such as an earphone. The sound-reproducing device includes a speaker, for receiving electrical signals representing a wanted sound, such as music or speech, from a portable music player, telephone handset, or the like. The noise cancellation system includes a microphone provided on the sound-reproducing device, to generate an electrical signal representing ambient noise. This ambient noise signal is then applied to signal processing circuitry to generate a noise cancellation signal, and the noise cancellation signal is applied to the speaker.

The purpose of the signal processing circuitry is to generate a noise cancellation signal that, when applied to the speaker, produces a sound that is equal in magnitude but opposite in phase to the ambient sounds reaching the user's ear. If this can be achieved, destructive interference will have the effect of reducing the noise that can be heard by the user.

In order to achieve this, it is known, for example from GB-2441835A, that the signal processing circuitry needs to apply frequency-selective filtering to the ambient noise signal, and that this frequency-selective filtering needs to take account of the frequency-dependent amplitude and phase characteristics of: the response of the noise microphone; any electronic amplification in the signal processing circuitry; and the response of the speaker. These characteristics are generally relatively stable for any given individual earphone device and, subject to manufacturing tolerances, they can be determined for any model of earphone.

In addition, however, the frequency-selective filtering needs to take account of two further factors, namely the frequency-dependent amplitude and phase characteristics of the acoustic path from the surroundings into the ear of the user, and the phase and frequency response of the acoustic path from the speaker to the ear of the user. These are both dependent on the leakage characteristics of the earphone, that is, the leakage in the coupling of the earphone to the ear of the wearer.

It is known that the frequency-dependent characteristics of the leakage path can vary widely, depending on how the sound-reproducing device interacts with the ear of the user. More specifically, one important factor is the area of the leakage, which affects both the amplitude and phase of all signals perceived by the ear. For example, in the case of an earphone that is intended to be worn within the outer ear of the user, the frequency-dependent leakage characteristics will depend on the exact shape of the user's ear, and on how tightly the earphone is pushed into the ear.

This has the effect that it is difficult to perform frequency-selective filtering that is sufficiently representative of the frequency-dependent amplitude and phase leakage characteristics.

SUMMARY OF THE INVENTION

According to a first aspect of the present invention, there is provided an earphone, for location in use in the concha of a user, wherein the earphone comprises:

- an earphone body, containing a speaker for generating sounds; and
- a projection, extending from a first surface of the earphone body, for location in or at the entrance to the ear canal of the user,
- wherein the projection contains a sound inlet port, connected to a microphone for detecting sounds entering the ear canal.

According to a second aspect of the present invention, there is provided a noise cancellation system, comprising:

- noise cancellation circuitry, for applying a frequency dependent filter characteristic and applying a gain to an input signal representing ambient noise, to generate a noise cancellation signal, wherein at least one of the frequency dependent filter characteristic and the gain is adaptive; and
- an earphone for location in use in the concha of a user, wherein the earphone comprises:
- an earphone body, containing a speaker for generating sounds, wherein the speaker is connected to the noise cancellation circuitry to receive the noise cancellation signal;
- an ambient noise microphone, for detecting ambient noise in the region of the earphone, and for supplying an ambient noise signal as an input to the noise cancellation circuitry; and
- a projection, extending from a first surface of the earphone body, for location in the ear canal of the user,
- wherein the projection contains a sound inlet port, connected to an error microphone for detecting sounds entering the ear canal, and for generating an error signal, wherein the error microphone is connected to the noise cancellation circuitry, and wherein the noise cancellation circuitry is configured to adapt at least one of the frequency dependent filter characteristic and the gain in response to the error signal According to a third aspect of the present invention, there is provided an earphone system, comprising:

- a jack, for plugging into a sound source; and
- at least one earphone according to the first aspect.

According to a fourth aspect of the present invention, there is provided a sound reproduction system, comprising a sound source, and an earphone system according to the third aspect.

This has the advantage that the amount of ambient noise that the error microphone can conveniently detect the sound entering the user's ear canal.

BRIEF DESCRIPTION OF THE DRAWINGS

For a better understanding of the present invention, and to show how it may be put into effect, reference will now be made, by way of example, to the accompanying drawings, in which.

DESCRIPTION OF THE PREFERRED EMBODIMENTS

Figure 1:
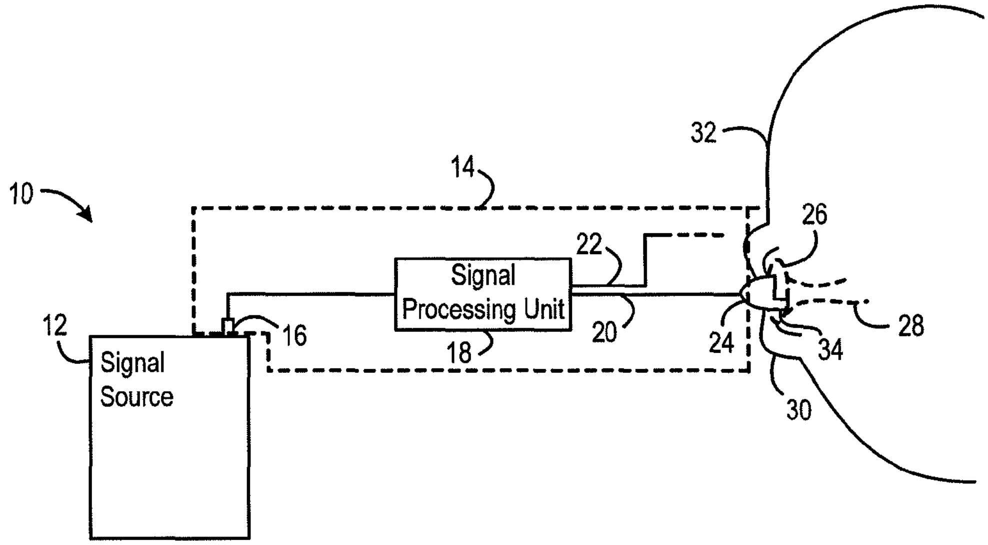
FIG. 1 illustrates the use of an earphone in accordance with an aspect of the present invention.

FIG. 1 shows a sound reproduction system 10, including a signal source 12 and an earphone system 14. The signal source 12 might be a playback device such as an MP3 player, or a device for receiving sound signals such a mobile phone handset, or the like.

The earphone system 14 may include a jack 16 that plugs into the signal source 12, and a signal processing unit 18. Although a separate signal processing unit 18 is shown in FIG. 1, the invention is equally applicable to systems in which the signal processing takes place within the signal source, or even within the earphones themselves.

In this example, the sound reproduction system 10 is a stereo system, and so the signal processing unit 18 includes respective leads 20, 22 connected to two earphones, of which only one earphone 24 is shown in FIG. 1, it being understood that the other earphone of the pair is simply a mirror image of the first. The leads 20, 22 may each be made up of several wires, allowing separate signals to be passed along them, as described in more detail below.

The earphone 24 is of a size and shape that allows it to fit within the concha 26 at the entrance to the ear canal 28 in the outer ear 30 of a user 32.

The earphone 24 includes a protruding guide piece 34, that extends from the front surface of the earphone, so that it can be located in or at the entrance to the ear canal 28 of the user.

Figure 2:
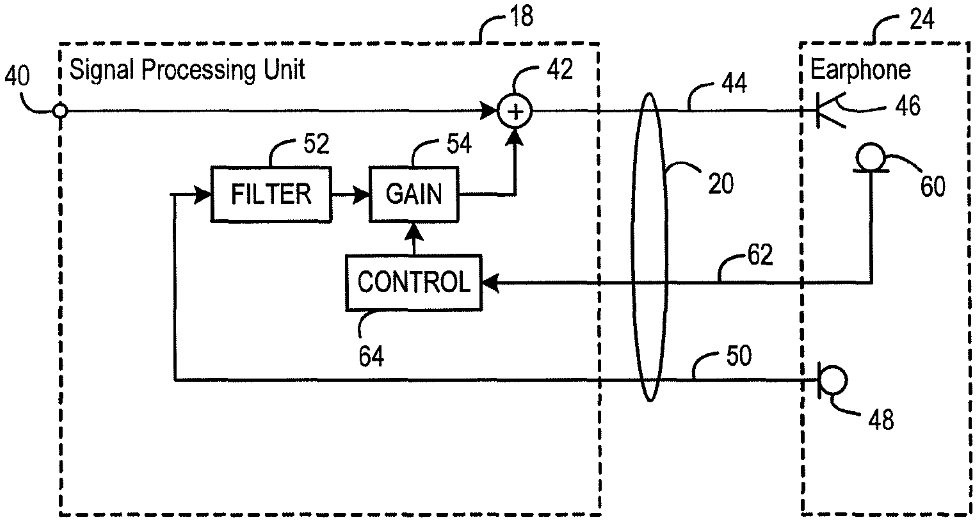
FIG. 2 shows a first noise cancellation system for use with the earphone of the present invention.

FIG. 2 shows the general form of the noise cancellation system within the sound reproduction system 10. Specifically, the signal processing unit 18 receives a wanted signal from the signal source 12 on an input 40. This might for example be the signal representing the speech or music that the user wishes to hear.

The wanted signal is applied to a first input of an adder 42, and the output from the adder 42 is output over a first wire 44 in the lead 20 to a speaker 46 in the earphone 24.

The earphone 24 also includes at least one microphone 48, for detecting ambient noise in the vicinity of the earphone. For example, the microphone 48 might be positioned in the rear surface of the earphone 24. Ambient noise signals from the microphone 48 may be passed along a second wire 50 in the lead 20 to the signal processing unit 18.

The ambient noise signals are passed to a filter 52, and to a gain unit 54 to generate a noise cancellation signal, which is applied to a second input of the adder 42, so that it is added to the wanted signal as the latter is supplied to the speaker 46.

If the signal processing performed by the filter 52 and gain unit 54 in the signal processing unit 18 can be controlled appropriately, then the effect of applying the noise cancellation signal to the speaker 46 is to generate a sound that will cancel out the ambient noise to at least some extent, thereby making the wanted sounds more clearly audible.

As is well known, effective noise cancellation requires that the filter characteristics of the filter 52 and the gain unit 54 should be well matched to the other characteristics of the system. Thus, the filter 52 can have a frequency response characteristic that compensates for any frequency dependent variations in the responses of the ambient noise microphone 48 or the loudspeaker 46. Also, the filter 52 can have a frequency response characteristic that compensates for any frequency dependent variations in the ambient noise that reaches the user's ear around the earphone as it is worn. These characteristics of the filter 52 can be preset, based on knowledge of the earphone 24 with which the signal processing unit 18 is to be used.

The system shown in FIG. 2 is an adaptive feedforward system, in which the ambient noise signals are passed through a fixed filter 52 and a controllable gain unit 54. In other embodiments, the filter 52 can be controllable and the gain unit 52 fixed, while, in still further embodiments, the filter 52 and gain unit 54 are both controllable.

Thus, the earphone 24 also includes an error microphone 60, positioned close to the speaker 46, so that, in use, it can detect sounds present at the entrance to the user's ear canal.

Signals generated by the error microphone 60 are passed signals along a third wire 62 in the lead 20 to a control block 64 in the signal processing unit 18.

As is known, the control block 64 might also receive other input signals, for example from the input 40, and/or from the noise microphone 48. Based on the input signals that it receives, the control block 64 adapts the gain applied by the gain unit 54 in order to optimise the noise cancellation. As mentioned previously, in other embodiments, the control block 64 can alternatively or additionally adapt the characteristics of the filter 52.

More specifically, in ideal conditions, the sound detected by the error microphone 60 should correspond exactly to the wanted sounds received on the input 40, with no contribution from the ambient noise. To the extent that the sound detected by the error microphone 60 does not correspond exactly to the wanted sounds received on the input 40, or that there is a contribution from the ambient noise, the filter 52 and/or the gain unit 54 can be controlled to reduce such errors.

An important factor in determining whether the noise cancellation system can cancel the ambient noise can be described as the leakiness of the earphone.

When the earphone 24 is held loosely in the concha 26 of the ear of the user, there is a relatively high leakage. That is, the earphone 24 provides a low acoustic resistance to ambient sounds reaching the ear canal 28 of the user, and a low acoustic resistance to sounds from the speaker 46 reaching the exterior. In such circumstances, a relatively high degree of noise cancellation is required, and so the gain value applied in the gain unit 54 to the ambient noise signals received from the noise microphone 48 must be relatively high, if effective noise cancellation is to be achieved.

When the earphone 24 is held tightly over the entrance to the ear canal 28 of the user, it provides a high acoustic resistance to ambient sounds reaching the ear canal, and similarly a high acoustic resistance to sounds from the speaker 46 reaching the ambient environment, and there is said to be a relatively low leakage. In such circumstances, there is less noise reaching the ear requiring cancellation, and so the gain value applied in the gain unit 54 to the ambient noise signals received from the noise microphone 48 must be relatively low, if acceptable noise cancellation is to be achieved.

In the illustrated embodiment, the gain value applied by the gain unit 54 is adjustable, and so it is necessary to select a gain value that provides an acceptable degree of noise cancellation, however the earphone is used by the user.

It is also true that the way in which the earphone 24 is worn in the concha 26 of the ear of the user will have an effect on the frequency characteristic of the sound leakage path, by which the ambient sounds reach the ear canal 28 of the user. Thus, in other embodiments of the invention, the frequency characteristic of the filter 52 is adapted based on the signal generated by the error microphone 60.

Figure 3:
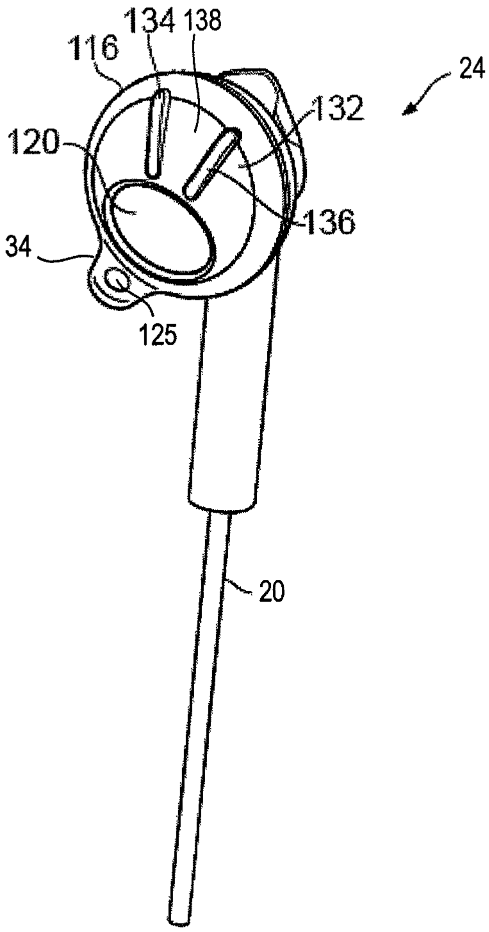
FIG. 3 is a perspective view, showing the form of an earphone in accordance with an aspect of the present invention.
Figure 4:
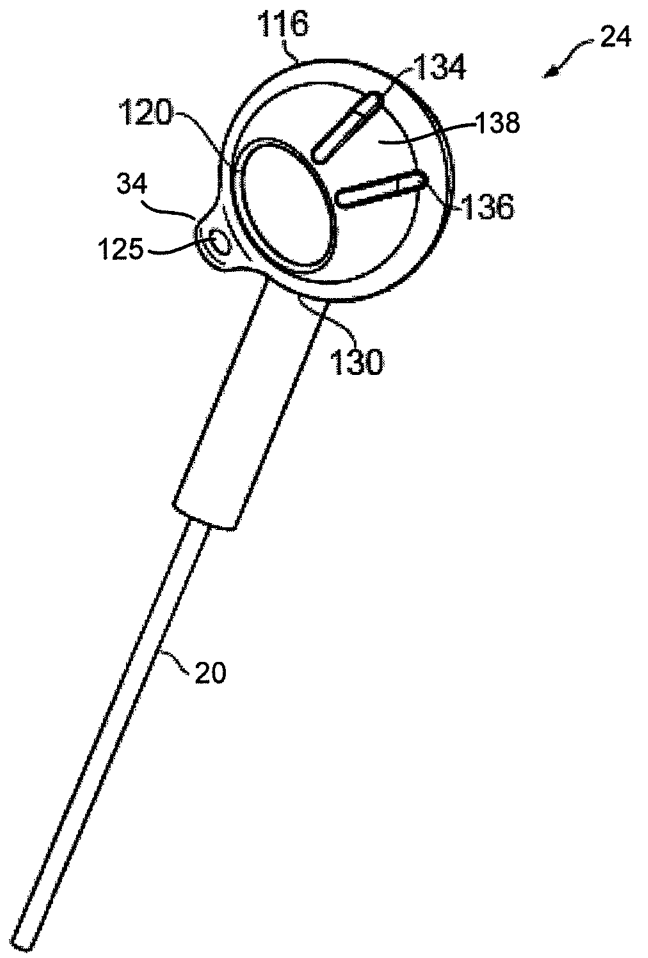
FIG. 4 is a front view, showing the earphone of FIG. 3.
Figure 5:
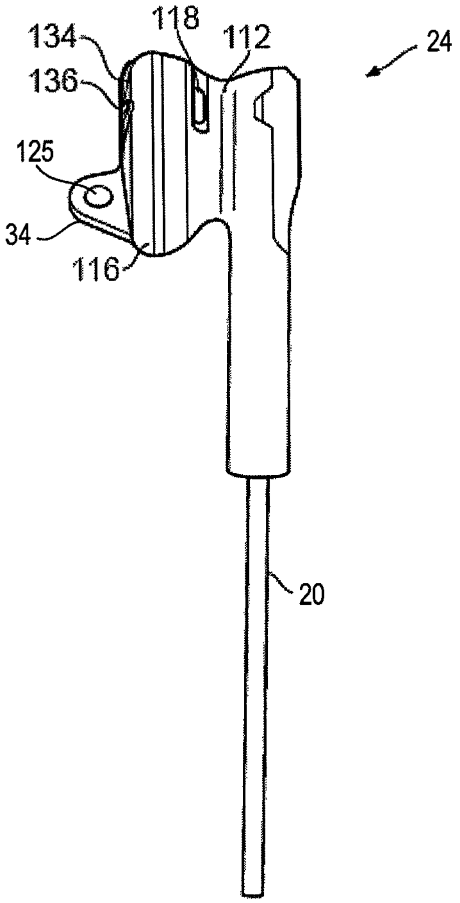
FIG. 5 is a side view, showing the earphone of FIG. 3.

FIGS. 3, 4 and 5 show a form of earphone, having a suitable error microphone, for detecting the sounds present at the entrance to the ear canal of the user.

Specifically, FIGS. 3, 4 and 5 show an earphone 24, having an earphone body in the form of a casing 112, which is of a size and shape that allows it to be placed in the outer ear of the user, adjacent to the entrance to the user's ear canal. Connected to the casing 112 is the lead 20. The casing 112 may be made of a rigid plastic material, or any other suitable material.

A cushion 116 is mounted around a first end region of the casing 112. The cushion 116 may be made of a material, such as plastic or rubber, that is less rigid, i.e. softer, than the casing body 112, and may be designed to be removable from the casing body 112 by slight stretching, so that it can be replaced if necessary. The cushion 116 acts as a gasket, providing a partial seal between the casing body 112 and the outer ear of the user, and allowing the earphone to be worn in comfort.

In other embodiments, the casing can have a unitary structure. That is, the casing body and the cushion can be formed as a single body.

The casing body 112 has one or more holes 118, allowing ambient sounds to enter the casing, so that they can be detected by the microphone 48 (not shown in FIGS. 3, 4 and 5). The, or each, hole 118 is preferably positioned away from the first end region of the casing body, so that it is not obstructed by the user's ear when the earphone is being worn.

The speaker 46 (not shown in FIGS. 3, 4 and 5) is mounted inside the casing 112, and is positioned and oriented so that it directs sound out of the casing through a sound outlet 120 in the surface 132 that is placed against the user's ear. The sound outlet 120 may comprise a hole in the casing 112 and cushion 116 that is covered by a sound-permeable but water-resistant material, such as a mesh.

The sound outlet 120 is positioned so that, when the earphone 24 is worn in the intended position, the sound outlet 120 is adjacent the entrance to the user's ear canal.

In order to assist in ensuring that the earphone 24 is worn in the intended position, a protruding guide piece 34 extends from the surface of the casing 116, adjacent to the sound outlet 120. For comfort, the user will naturally adjust the position of the earphone so that the guide piece 34 lies in the entrance to the ear canal, and this will automatically cause the sound outlet 120 to lie adjacent to the entrance to the ear canal.

The guide piece 34 has a sound inlet hole 125, and the error microphone 60 (not shown in FIGS. 3, 4 and 5) is mounted either behind the sound inlet hole 125 or inside the casing 116 in such a position that it can detect sound entering through the sound inlet hole 125 and passing along a suitably designed sound channel.

Thus, the positioning of the sound inlet hole 125 is such that the error microphone 60 can detect sounds at the entrance to the user's ear canal.

As described above, the signal generated by the error microphone 60 is used in this embodiment to adapt the gain of the signal processing unit 18 to the amount of sound leakage past the earphone 24 when it is worn in the user's ear. In the embodiment shown in FIGS. 3, 4 and 5, this adaptation is made easier by the fact that the structure of the earphone 24 means that the range of leakage values is restricted, despite differences in how the earphone might be worn in the ear of the user.

Thus, provided on the surface 132 of the earphone are two ridges 134, 136 that define a sound channel 138 between them. The ridges have sufficient stiffness that, even if the earphone 24 is pressed moderately tightly against the user's ear, the sound channel 138 will still be sufficient to allow a degree of leakage of the ambient sound into the user's ear canal.

This means that the range of leakage values is restricted, and hence that the necessary range, within which the gain of the signal processing unit 18 needs to be adapted, is similarly restricted. This makes it easier to provide the optimum amount of gain, and hence that the noise cancellation effect is improved.

Similarly, the restriction of the range of leakage values means that the range, within which the frequency characteristic of the signal processing unit 18 needs to be adapted, is also restricted. In this illustrated embodiment, the noise cancellation effect is adequate without any adaptation of the frequency characteristic.

Figure 6:
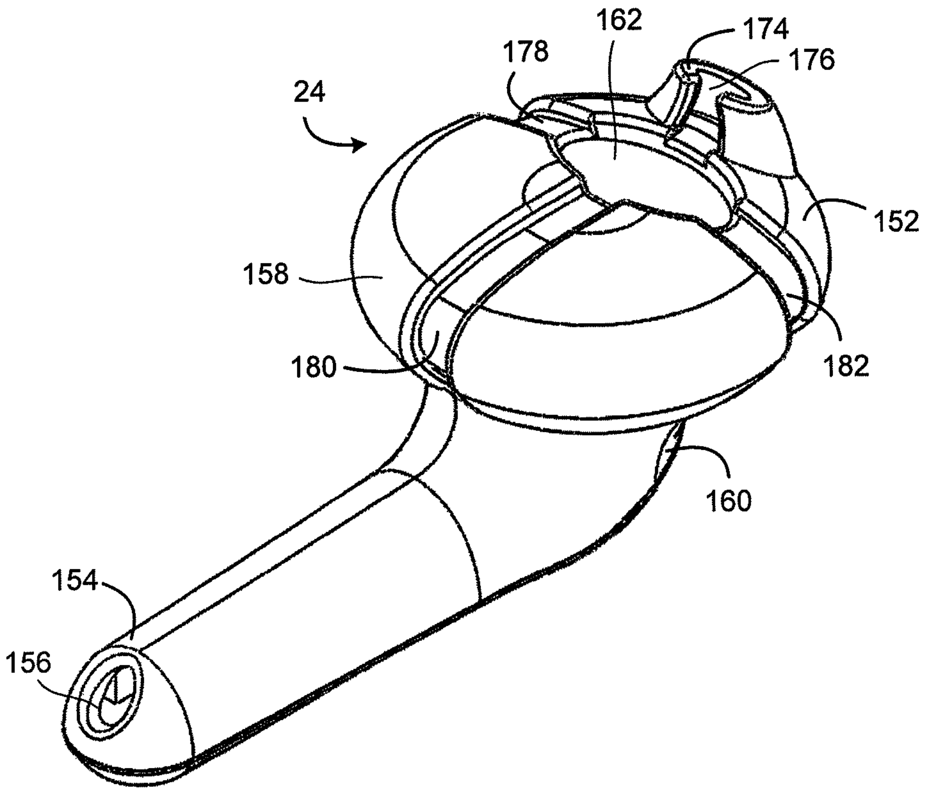
FIG. 6 is a perspective view, showing an alternative the form of the earphone in accordance with an aspect of the present invention.

FIG. 6 shows an alternative embodiment of an earphone 24 in accordance with the invention.

The earphone 24 shown in FIG. 6 has an earphone body in the form of a casing with a first end region 152, which is of a size and shape that allows it to be placed in the outer ear of the user, adjacent to the entrance to the user's ear canal. The casing also has a second end region 154, having a hole 156 from which the lead 20 (not shown in FIG. 6) can protrude. The first end region 152 of the casing may be made of a rigid plastic material, or any other suitable material.

A cushion 158 is mounted around the first end region 152 of the casing. The cushion 158 may be made of a material, such as plastic or rubber, that is less rigid, i.e. softer, than the casing, and may be designed to be removable from the casing by slight stretching, so that it can be replaced if necessary. The cushion 158 acts as a gasket, providing a partial seal between the casing and the outer ear of the user, and allowing the earphone to be worn in comfort.

In other embodiments, the casing can have a unitary structure. That is, the first end region 152 of the casing and the cushion can be formed as a single body.

The first end region 152 of the casing has one or more holes 160, allowing ambient sounds to enter the casing, so that they can be detected by the microphone 48 (not shown in FIG. 6). The, or each, hole 160 is preferably positioned on the rear side of the first end region 152 of the casing body, so that it is not obstructed by the user's ear when the earphone is being worn.

The speaker 46 (not shown in FIG. 6) is mounted inside the casing, and is positioned and oriented so that it directs sound out of the casing through a sound outlet 162 in the front side of the first end region 152 of the casing body. The sound outlet 162 may comprise a hole in the casing and the cushion 158 that is covered by a sound-permeable but water-resistant material, such as a mesh.

The sound outlet 162 is positioned so that, when the earphone 24 is worn in the intended position, the sound outlet 162 is adjacent the entrance to the user's ear canal.

In order to assist in ensuring that the earphone 24 is worn in the intended position, a protruding guide piece 34, in the form of a curved structure 174 having an approximately C-shaped cross-section, extends from the front side surface of the first end region 152 of the casing body, adjacent to the sound outlet 162. For comfort, the user will naturally adjust the position of the earphone so that the guide structure 174 lies in the entrance to the ear canal, and this will automatically cause the sound outlet 162 to lie adjacent to the entrance to the ear canal.

The guide structure 174 has a sound inlet hole 176, and the error microphone 60 (not shown in FIG. 6) can be mounted in the guide structure 174. Alternatively, a passage can connect the sound inlet hole 176 to the error microphone 60, which can then be located inside the first end region 152 of the casing (or elsewhere in the casing).

Thus, in any of these positions of the error microphone 60, sound at the entrance to the user's ear canal can enter through the sound inlet hole 176 and be detected by the error microphone 60.

As described above, the signal generated by the error microphone 60 is used in this embodiment to adapt the gain of the signal processing unit 18 to the amount of sound leakage past the earphone 24 when it is worn in the user's ear. In the embodiment shown in FIG. 6, this adaptation is made easier by the fact that the structure of the earphone 24 means that the range of leakage values is restricted, despite differences in how the earphone might be worn in the ear of the user.

Thus, provided in the cushion 158 are three sound channels 178, 180, 182. The cushion 158 is compliant enough to be worn in comfort by a range of users, but has enough stiffness that, even if the earphone 24 is pressed moderately tightly against the user's ear, the sound channels 178, 180, 182 will still be sufficient to allow a degree of leakage of the ambient sound into the user's ear canal.

As described above, this means that the range of leakage values is restricted, and hence that the necessary range, within which the gain of the signal processing unit 18 needs to be adapted, is similarly restricted. This makes it easier to provide the optimum amount of gain, and hence that the noise cancellation effect is improved. Similarly, the restriction of the range of leakage values means that the range, within which the frequency characteristic of the signal processing unit 18 needs to be adapted, is also restricted. In this illustrated embodiment, the noise cancellation effect is adequate without any adaptation of the frequency characteristic.

In certain embodiments of the present invention, a microphone is located in an earphone, such that it is able to detect sounds entering the ear canal of the wearer of the earphone. In the illustrated embodiments, the signals generated by the microphone are used as inputs to a noise cancellation system. However, in other embodiments of the invention, the signals generated by the microphone are used as inputs to other control systems or circuits.

For example, the signal detected by the error microphone 60 can be supplied to a loudness limiter function, to ensure that the sound volume reaching the user's ear does not exceed a limit that is specified on grounds of comfort or safety. If the signal detected by the error microphone exceeds that limit, the sounds being played through the speaker 48 can then be limited.

As another example, it has been appreciated that the signal detected by the error microphone 60 can be used as an indicator of how the earphone 24 is being worn in the user's ear. In a sound reproduction system, signals representing wanted sounds such as speech or music are passed through a signal equaliser, which is able to apply frequency selective gain to the signals. The equalisation will attempt to compensate for any frequency dependent properties of the listening system being used by the listener. In the case of a listening system in the form of an earphone, the frequency dependent properties of the listening system will depend for example on how tightly the earphone is pressed into the user's ear. Typically, the designer of the sound reproduction system will not know how the earphone will be worn, and will have to set an equalisation profile that assumes a typical use. In this case, the signal detected by the error microphone can be used as a measure of the amount of ambient noise leaking past the earphone, and thus can be used as a measure of the frequency dependent properties of the listening system, as they depend on the way in which the earphone is pressed into the user's ear. Thus, the signal detected by the error microphone can be used as an input into the equalisation device, and can be used to control the frequency selective signal equalisation.

It will be apparent that, in either of these examples, the error microphone can be located in any convenient position for detecting sounds in or at the entrance to the user's ear canal.

It will also be apparent that the loudness limiter function and the leakage dependent adaptive signal equalisation can be provided in systems that do not use noise cancellation, provided that there is a microphone suitably positioned for detecting sounds in or at the entrance to the user's ear canal.

There are thus described earphones that allow accurate measurements of the sound leakage past the earphone into the user's ear canal.

What is claimed is:

1. An earphone, for location in use in the concha of a user, wherein the earphone comprises:

an earphone body, containing a speaker for generating sounds, wherein the earphone body comprises a sound outlet in a first surface thereof, for allowing sounds generated by the speaker to leave the earphone body; and a projection, extending from the first surface of the earphone body, adjacent to the sound outlet, for location in or at the entrance to the ear canal of the user, wherein the projection contains a sound inlet port, connected to a microphone for detecting sounds entering the ear canal; and wherein the microphone for detecting sounds entering the ear canal is located within said projection.

2. An earphone as claimed in claim 1, comprising at least one sound channel provided at the first surface of the earphone body.

3. An earphone as claimed in claim 2, comprising a plurality of ridges formed on the first surface of the earphone body, and defining the at least one sound channel between the ridges.

4. An earphone as claimed in claim 2, wherein the at least one sound channel is formed in the first surface of the earphone body.

5. An earphone as claimed in claim 1, comprising an ambient noise microphone, for detecting ambient noise in the region of the earphone.

6. An earphone as claimed in claim 5, wherein the earphone body comprises a sound inlet hole in a surface thereof separate from the first surface, and wherein the ambient noise microphone is positioned to detect sound entering through the sound inlet hole.

7. A noise cancellation system, comprising:

noise cancellation circuitry, for applying a frequency dependent filter characteristic and applying a gain to an input signal representing ambient noise, to generate a noise cancellation signal, wherein at least one of the frequency dependent filter characteristic and the gain is adaptive; and an earphone for location in use in the concha of a user, as claimed in claim 1, wherein the speaker of the earphone is connected to the noise cancellation circuitry to receive the noise cancellation signal; and wherein the earphone further comprises:

an ambient noise microphone, for detecting ambient noise in the region of the earphone, and for supplying an ambient noise signal as an input to the noise cancellation circuitry; and wherein the sound inlet port contained in the projection of the earphone is connected to an error microphone which is adapted to generate an error signal, wherein the error microphone of the earphone for detecting sounds entering the ear canal is connected to the noise cancellation circuitry, and wherein the noise cancellation circuitry is configured to adapt at least one of the frequency dependent filter characteristic and the gain in response to the error signal.

8. A noise cancellation system as claimed in claim 7, wherein the earphone comprises at least one sound channel provided at the first surface of the earphone body.

9. A noise cancellation system as claimed in claim 8, comprising a plurality of ridges formed on the first surface of the earphone body, and defining the at least one sound channel between the ridges.

10. A noise cancellation system as claimed in claim 8, wherein the at least one sound channel is formed in the first surface of the earphone body.

11. A noise cancellation system as claimed in claim 7, wherein the microphone for detecting sounds entering the ear canal is located within said projection.

12. An earphone system, comprising:

a jack, for plugging into a sound source; and at least one earphone as claimed in claim 1.

13. An earphone system as claimed in claim 12, comprising a pair of the earphones.

14. A sound reproduction system, comprising a sound source, and an earphone system as claimed in claim 12.

15. An earphone, for location in use in the concha of a user, wherein the earphone comprises:

an earphone body, containing a speaker for generating sounds, wherein the earphone body comprises a sound outlet in a first surface thereof, for allowing sounds generated by the speaker to leave the earphone body; and a projection, extending from the first surface of the earphone body, adjacent to the sound outlet, for location in or at the entrance to the ear canal of the user, wherein the projection contains a sound inlet port, separated from the sound outlet, connected to a microphone for detecting sounds entering the ear canal.

16. An earphone as claimed in claim 15 wherein the error microphone is in such a position that it can detect sound entering through the sound inlet port and passing along a suitably designed sound channel.

17. An earphone as claimed in claim 15, comprising at least one sound channel provided at the first surface of the earphone body.

18. An earphone as claimed in claim 17, comprising a plurality of ridges formed on the first surface of the earphone body, and defining the at least one sound channel between the ridges.

19. An earphone as claimed in claim 17, wherein the at least one sound channel is formed in the first surface of the earphone body.

20. An earphone as claimed in claim 15, comprising an ambient noise microphone, for detecting ambient noise in the region of the earphone.

21. An earphone as claimed in claim 20, wherein the earphone body comprises a sound inlet hole in a surface thereof separate from the first surface, and wherein the ambient noise microphone is positioned to detect sound entering through the sound inlet hole.

22. An earphone as claimed in claim 20, wherein the microphone for detecting sounds entering the ear canal is located within said projection.

23. An earphone, for location in use in the concha of a user, wherein the earphone comprises:

an earphone body, containing a speaker for generating sounds, wherein the earphone body comprises a sound outlet in a first surface thereof, for allowing sounds generated by the speaker to leave the earphone body; and a projection, extending from the first surface of the earphone body, adjacent to the sound outlet, for location in or at the entrance to the ear canal of the user, wherein the projection contains a sound inlet port, connected to a microphone for detecting sounds entering the ear canal, wherein the earphone body comprises a plurality of ridges defining at least one sound channel between the ridges.

24. An earphone as claimed in claim 23, comprising an ambient noise microphone, for detecting ambient noise in the region of the earphone.

25. An earphone as claimed in claim 24, wherein the earphone body comprises a sound inlet hole in a surface thereof separate from the first surface, and wherein the ambient noise microphone is positioned to detect sound entering through the sound inlet hole.

26. An earphone as claimed in claim 23, wherein the microphone for detecting sounds entering the ear canal is located within said projection.

27. A noise cancellation system, comprising:

noise cancellation circuitry, for applying a frequency dependent filter characteristic and applying a gain to an input signal representing ambient noise, to generate a noise cancellation signal, wherein at least one of the frequency dependent filter characteristic and the gain is adaptive; and an earphone for location in use in the concha of a user as claimed in claim 15, wherein the speaker of the earphone is connected to the noise cancellation circuitry to receive the noise cancellation signal;

wherein the earphone further comprises an ambient noise microphone for detecting ambient noise in the region of the earphone, and for supplying an ambient noise signal as an input to the noise cancellation circuitry; and wherein the sound inlet port contained in the projection of the earphone is connected to an error microphone which is adapted to generate an error signal, wherein the error microphone of the earphone for detecting sounds entering the ear canal is connected to the noise cancellation circuitry, and wherein the noise cancellation circuitry is configured to adapt at least one of the frequency dependent filter characteristic and the gain in response to the error signal.

28. A noise cancellation system as claimed in claim 27, wherein the earphone comprises at least one sound channel provided at the first surface of the earphone body.

29. A noise cancellation system as claimed in claim 28, comprising a plurality of ridges formed on the first surface of the earphone body, and defining the at least one sound channel between the ridges.

30. A noise cancellation system as claimed in claim 28, wherein the at least one sound channel is formed in the first surface of the earphone body.

31. A noise cancellation system as claimed in claim 27, wherein the microphone for detecting sounds entering the ear canal is located within said projection.

32. A noise cancellation system, comprising:

noise cancellation circuitry, for applying a frequency dependent filter characteristic and applying a gain to an input signal representing ambient noise, to generate a noise cancellation signal, wherein at least one of the frequency dependent filter characteristic and the gain is adaptive; and an earphone for location in use in the concha of a user as claimed in claim 23, wherein the speaker of the earphone is connected to the noise cancellation circuitry to receive the noise cancellation signal;

wherein the earphone further comprises an ambient noise microphone for detecting ambient noise in the region of the earphone, and for supplying an ambient noise signal as an input to the noise cancellation circuitry; and wherein the sound inlet port contained in the projection of the earphone is connected to an error microphone which is adapted to generate an error signal, wherein the error microphone of the earphone for detecting sounds entering the ear canal is connected to the noise cancellation circuitry, and wherein the noise cancellation circuitry is configured to adapt at least one of the frequency dependent filter characteristic and the gain in response to the error signal.

33. A noise cancellation system as claimed in claim 32, wherein the at least one sound channel is formed in the first surface of the earphone body.

34. A noise cancellation system as claimed in claim 33, wherein the microphone for detecting sounds entering the ear canal is located within said projection.

* * * * *